United States Patent
Ishii et al.

(10) Patent No.: US 11,291,372 B2
(45) Date of Patent: Apr. 5, 2022

(54) LASER DEVICE AND PHOTOACOUSTIC MEASUREMENT APPARATUS

(71) Applicant: FUJIFILM Corporation, Tokyo (JP)

(72) Inventors: Hiroyasu Ishii, Kanagawa (JP); Kazuhiro Hirota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 694 days.

(21) Appl. No.: 16/142,297

(22) Filed: Sep. 26, 2018

(65) Prior Publication Data

US 2019/0021603 A1 Jan. 24, 2019

Related U.S. Application Data

(63) Continuation of application No. PCT/JP2017/007632, filed on Feb. 28, 2017.

(30) Foreign Application Priority Data

Mar. 30, 2016 (JP) .............................. JP2016-067327

(51) Int. Cl.
*H01S 3/115* (2006.01)
*A61B 5/00* (2006.01)
(Continued)

(52) U.S. Cl.
CPC ....... *A61B 5/0095* (2013.01); *G01N 29/2418* (2013.01); *G01N 29/44* (2013.01);
(Continued)

(58) Field of Classification Search
CPC .......... H01S 3/136; H01S 3/115; H01S 3/061; H01S 3/08054; H01S 3/092;
(Continued)

(56) References Cited

U.S. PATENT DOCUMENTS 1,694,661 A * 12/1928 Meissner .............. G02F 1/0131
358/302
3,694,769 A * 9/1972 Hook ...................... H01S 3/115
372/12
(Continued)

FOREIGN PATENT DOCUMENTS

CN 201278434 Y 7/2009
CN 101882749 A 11/2010
(Continued)

OTHER PUBLICATIONS

Chinese Office Action and Search Report dated Nov. 5, 2019, for Chinese Patent Application No. 201780020782.7, with partial translation.
(Continued)

*Primary Examiner* — Tod T Van Roy
*Assistant Examiner* — Delma R Fordé
(74) *Attorney, Agent, or Firm* — Birch, Stewart, Kolasch & Birch, LLP

(57) ABSTRACT

In a laser device that emits pulsed laser light by emitting excitation light to a laser medium in a state in which a first voltage is applied to a Q switch and changing the voltage applied to the Q switch from a first voltage to a second voltage after the emission of the excitation light, the application start timing of the first voltage during a normal operation is set to a timing at which the intensity of the pulsed laser light periodically changing due to the vibration of the Q switch is maximized.

13 Claims, 8 Drawing Sheets

(51) Int. Cl.
*H01S 3/10* (2006.01)
*G01N 29/24* (2006.01)
*G01N 29/44* (2006.01)
*H01S 3/136* (2006.01)
*H01S 3/06* (2006.01)
*H01S 3/08* (2006.01)
*H01S 3/092* (2006.01)
*H01S 3/16* (2006.01)

(52) U.S. Cl.
CPC .......... *H01S 3/10046* (2013.01); *H01S 3/115* (2013.01); *H01S 3/136* (2013.01); *A61B 5/7225* (2013.01); *A61B 2576/00* (2013.01); *H01S 3/061* (2013.01); *H01S 3/08054* (2013.01); *H01S 3/092* (2013.01); *H01S 3/10069* (2013.01); *H01S 3/1633* (2013.01)

(58) Field of Classification Search
CPC . H01S 3/1109; A61B 5/0095; G01N 29/2418; G02F 1/0131; G02F 1/0154; G02F 1/03–076
See application file for complete search history.

(56) References Cited

U.S. PATENT DOCUMENTS

| | | | | |
|---|---|---|---|---|
| 4,375,684 | A | 3/1983 | Everett | |
| 5,394,415 | A * | 2/1995 | Zucker | G02F 1/0126 372/10 |
| 10,105,063 | B2 * | 10/2018 | Hirota | H01S 3/005 |
| 10,243,317 | B2 * | 3/2019 | Ishii | H01S 3/107 |
| 10,243,318 | B2 * | 3/2019 | Murakoshi | H01S 3/0809 |
| 2014/0376574 | A1 * | 12/2014 | Skrabelj | G02F 1/0327 372/12 |
| 2015/0207292 | A1 * | 7/2015 | Jonuska | H01S 3/091 372/12 |
| 2016/0226214 | A1 | 8/2016 | Ishii et al. | |
| 2017/0012403 | A1 * | 1/2017 | Murakoshi | H01S 3/0809 |
| 2019/0021604 | A1 * | 1/2019 | Ishii | H01S 3/136 |
| 2020/0099191 | A1 * | 3/2020 | Hirota | A61B 8/13 |

FOREIGN PATENT DOCUMENTS

| | | |
|---|---|---|
| CN | 103346742 A | 10/2013 |
| GB | 1166922 A | 10/1969 |
| JP | 59-104558 U | 7/1984 |
| JP | 1-70372 U | 5/1989 |
| JP | 5-299752 A | 11/1993 |
| JP | 9-181375 A | 7/1997 |
| JP | 10-247755 A | 9/1998 |
| JP | 2005-268415 A | 9/2005 |
| JP | 2015-111660 A | 6/2015 |
| JP | 2015-525003 A | 8/2015 |

OTHER PUBLICATIONS

International Preliminary Report on Patentability and Written Opinion of the International Searching Authority (forms PCT/IB/373, PCT/ISA/237 and PCT/IB/326), dated Oct. 11, 2018, for corresponding International Application No. PCT/JP2017/007632, with an English translation of the Written Opinion.

International Search Report (form PCT/ISA/210), dated May 9, 2017, for corresponding International Application No. PCT/JP2017/007632, with an English translation.

Japanese Notice of Reasons for Refusal dated Jun. 4, 2019, for Japanese Patent Application No. 2018-508817, with English Translation.

* cited by examiner

FIG. 6
I FL TRIGGER
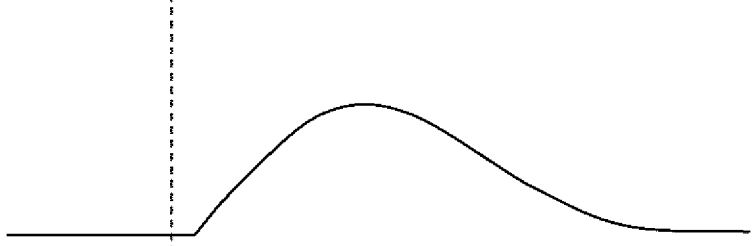
II FL CURRENT
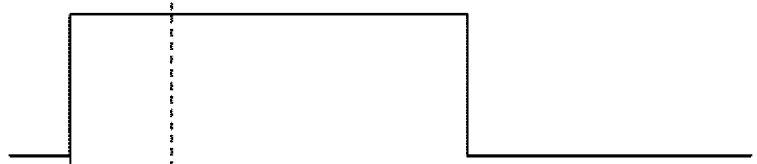
III Qsw VOLTAGE
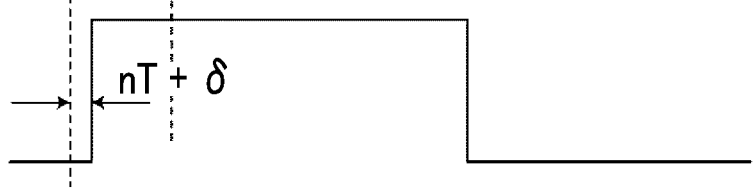
IV Qsw VOLTAGE
(PHASE SHIFT)
$nT + \delta$

LASER DEVICE AND PHOTOACOUSTIC MEASUREMENT APPARATUS

CROSS-REFERENCE TO RELATED APPLICATIONS

This application is a continuation application of International Application No. PCT/JP2017/007632, filed Feb. 28, 2017, the disclosure of which is incorporated herein by reference in its entirety. Further, this application claims priority from Japanese Patent Application No. 2016-067327, filed Mar. 30, 2016, the disclosure of which is incorporated herein by reference in its entirety.

BACKGROUND

1. Technical Field

The present invention relates to a laser device and more particularly, to a laser device that emits pulsed laser light as a giant pulse by resonating laser light emitted from a laser medium with a resonator. In addition, the present invention relates to a photoacoustic measurement apparatus including such a laser device.

2. Related Art

As a kind of image examination method capable of examining the state of the inside of the living body in a non-invasive manner, an ultrasound examination method is known. In ultrasound examination, an ultrasound probe capable of transmitting and receiving ultrasound waves is used. In a case where ultrasound waves are transmitted to a subject (living body) from the ultrasound probe, the ultrasound waves propagate through the living body and are reflected on the tissue interface. By receiving the reflected ultrasound waves using the ultrasound probe and calculating the distance based on the time until the reflected ultrasound waves return to the ultrasound probe, it is possible to image the state of the inside.

In addition, photoacoustic imaging for imaging the inside of the living body using the photoacoustic effect is known. In general, in the photoacoustic imaging, pulsed laser light, such as a laser pulse, is emitted into the living body. In the living body, the living tissue absorbs the energy of the pulsed laser light, and ultrasound waves (photoacoustic signal) are generated by adiabatic expansion due to the energy. By detecting the photoacoustic signal using an ultrasound probe or the like and forming a photoacoustic image based on the detected signal, it is possible to visualize the inside of the living body based on the photoacoustic signal.

For measurement of photoacoustic waves, it is necessary to emit pulsed laser light with high intensity in many cases. As a light source, a solid state laser device that emits pulsed laser light as a giant pulse by performing Q switch pulse oscillation is used in many cases. The laser device has a laser rod (laser medium) and a flash lamp (excitation light source) for exciting the laser rod. The laser device has a Q switch for Q switch pulse oscillation. A laser device that can be used for photoacoustic measurement is disclosed in, for example, JP2005-268415A or JP1993-299752A (JP-H05-299752A).

SUMMARY

In a case where a voltage applied to an electro-optical element used as a Q switch changes, the crystal of the electro-optical element is deformed, and the characteristics of the crystal change with time. As a result, an adverse effect, such as a reduction in the output of pulsed laser light, occurs. JP2005-268415A discloses a method for suppressing the adverse effect.

JP1993-299752A (JP-H05-299752A) also describes vibration (expressed as sound waves in JP1993-299752A (JP-H05-299752A)) generated due to deformation of the electro-optical element. Since such a vibration results in a reduction in the output of the pulsed laser light, JP1993-299752A (JP-H05-299752A) discloses a method for suppressing the vibration of the electro-optical element.

Thus, it is known that the vibration generated in the case of changing the voltage applied to the electro-optical element used as a Q switch causes a reduction in the output of the pulsed laser light. Conventionally, countermeasures have been taken to reduce the adverse effect due to the vibration of the Q switch.

Contrary to the conventional countermeasures, it is an object of the present invention to provide a laser device having improved output of pulsed laser light by actively using the vibration of the Q switch, which has been considered to have an adverse effect in the related art, and a photoacoustic measurement apparatus including the laser device.

A laser device of the present invention comprises: an excitation light source that emits excitation light; a laser medium that receives the excitation light emitted from the excitation light source and emits laser light; a resonator that includes a pair of mirrors with the laser medium interposed therebetween and that emits pulsed laser light by resonating the laser light between the pair of mirrors; a Q switch that is disposed on an optical path of the resonator to change a Q value of the resonator according to an applied voltage and that makes a Q value of the resonator in a case where a first voltage is applied lower than a Q value of the resonator in a case where a second voltage different from the first voltage is applied; a Q switch driving unit that drives the Q switch by applying the first voltage and the second voltage to the Q switch; and a controller that controls the excitation light source and the Q switch driving unit to emit the excitation light to the laser medium in a state in which the first voltage is applied to the Q switch and change a voltage applied to the Q switch from the first voltage to the second voltage after the emission of the excitation light such that the pulsed laser light is emitted. During a normal operation, the controller applies the first voltage to vibrate the Q switch and applies the second voltage to the Q switch at a timing at which a preset delay time has passed from start of the emission of the excitation light. An application start timing of the first voltage during the normal operation is set to a timing at which an intensity of the pulsed laser light periodically changing due to vibration of the Q switch is maximized in a case where the preset application start timing of the first voltage is changed with a preset time width.

In the laser device of the present invention, it is preferable that the preset application start timing of the first voltage is the same as an emission start timing of the excitation light.

It is preferable that the delay time is set to a time at which the intensity of the pulsed laser light is maximized in a case where, during a calibration operation different from the normal operation, the Q switch is vibrated by applying the first voltage, emission of the excitation light is started after an influence of the vibration of the Q switch disappears, and then a time until the second voltage is applied to the Q switch is changed.

It is preferable that the preset time width is the same time as a period of an intensity change of the pulsed laser light in a case where the application start timing of the first voltage is changed.

The first voltage may be a voltage higher than the second voltage.

The rise time of the first voltage is preferably 2 μs or less, and more preferably 1 μs or less.

The laser device may further comprise a storage unit that stores characteristic information indicating characteristics of a periodic change in the intensity of the pulsed laser light due to vibration of the Q switch in a case where the application start timing of the first voltage is changed.

The laser device may further comprise a display controller that displays the characteristic information stored in the storage unit on a display unit.

The laser device may further comprise a detection unit that detects a periodic change in the intensity of the pulsed laser light.

The laser device may further comprise a timing changing unit that receives a change in the application start timing of the first voltage during the normal operation.

A photoacoustic measurement apparatus of the present invention comprises: the laser device of the present invention described above; and a probe that detects photoacoustic waves generated in a subject due to emission of laser light from the laser device and outputs a photoacoustic wave signal.

The photoacoustic measurement apparatus of the present invention may further comprise an acoustic image generation unit that generates a photoacoustic image based on the photoacoustic wave signal output from the probe.

The probe may detect a reflected wave of an acoustic wave transmitted to the subject and output a reflected wave signal, and the acoustic image generation unit may generate a reflected acoustic image based on the reflected wave signal.

According to the laser device and the photoacoustic measurement apparatus of the present invention, during the normal operation, the Q switch is vibrated by applying the first voltage, and the second voltage is applied to the Q switch at the timing at which the preset delay time has passed from start of the emission of the excitation light. The application start timing of the first voltage during the normal operation is set to the timing at which the intensity of the pulsed laser light periodically changing due to vibration of the Q switch is maximized in a case where the preset application start timing of the first voltage is changed with the preset time width. Therefore, the output of the pulsed laser light can be made higher than in a case where vibration is not generated in the Q switch.

BRIEF DESCRIPTION OF THE DRAWINGS

Exemplary embodiments according to the technique of the present disclosure will be described in detail based on the following figures, wherein:

FIG. 6 is a timing chart showing the operation waveform of each component after timing adjustment of the laser device shown in FIG. 1;

DESCRIPTION

Figure 1:
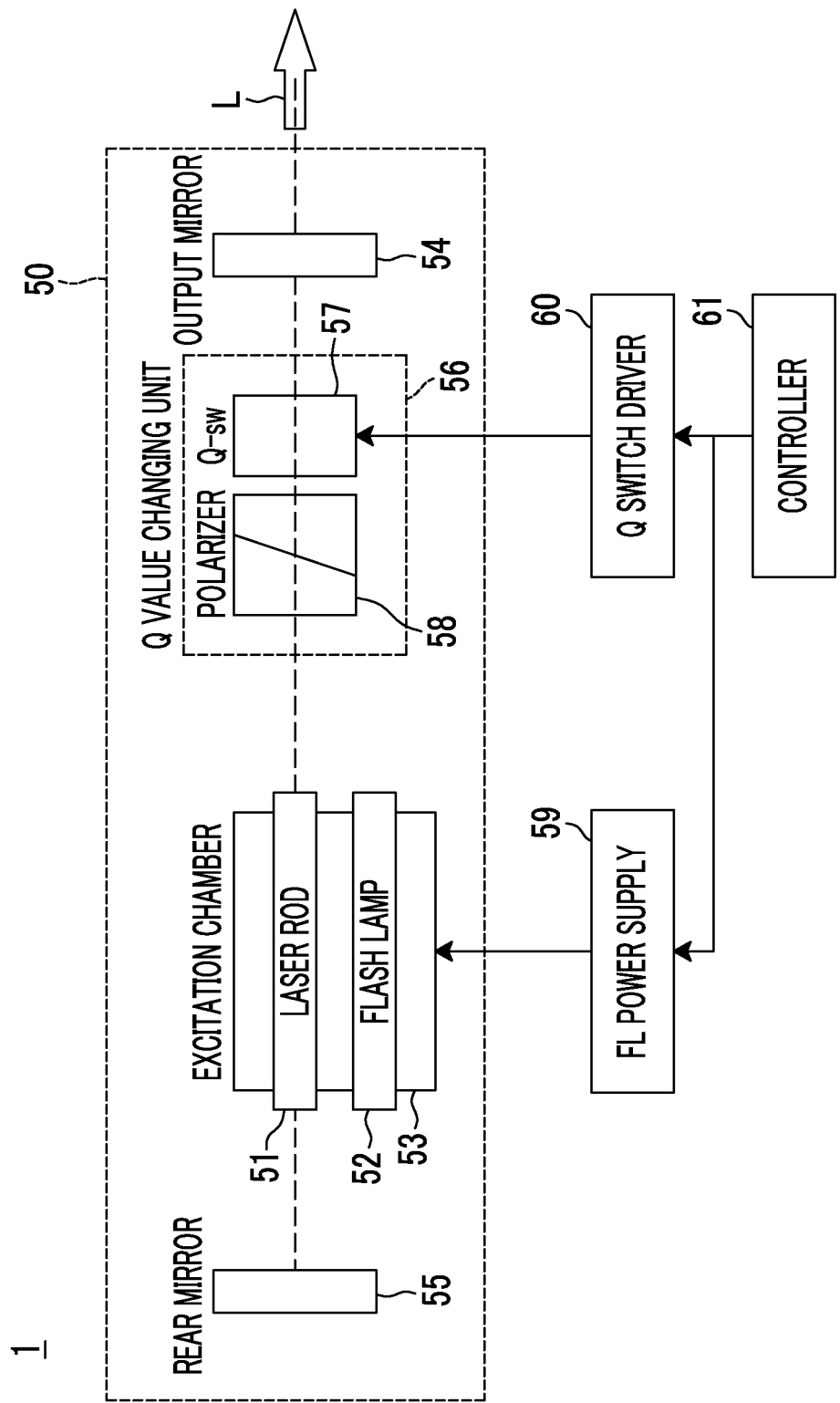
FIG. 1 is a block diagram showing a laser device of a first embodiment of the present invention.

Hereinafter, embodiments of the present invention will be described in detail with reference to the diagrams. FIG. 1 is a block diagram showing a laser device of a first embodiment of the present invention.

As shown in FIG. 1, a laser device 1 of the first embodiment includes a pulsed laser light emission unit 50 configured to include a laser rod 51, a flash lamp 52, an output mirror 54, a rear mirror 55, and a Q value changing unit 56, a flash lamp power supply 59, a Q switch driver 60, and a controller 61.

The laser rod 51 is a laser medium. As the laser rod 51, for example, alexandrite crystal is used. Light emitted from the laser rod 51 has a predetermined polarization axis. The flash lamp 52 is an excitation light source, and emits excitation light to the laser rod 51. A light source other than the flash lamp 52 may be used as the excitation light source. The laser rod 51 and the flash lamp 52 may be housed in an excitation chamber 53 as shown in FIG. 1. By adopting such a configuration, the laser rod 51 can be efficiently excited by the excitation light emitted from the flash lamp 52.

The output mirror 54 and the rear mirror 55 face each other with the laser rod 51 interposed therebetween, and a resonator is formed by the output mirror 54 and the rear mirror 55. The optical path in the resonator does not necessarily need to be linear, and the optical axis may be bent by providing a prism or the like on the optical path between the output mirror 54 and the rear mirror 55. The output mirror 54 is an output coupler (OC), and laser light is emitted from the output mirror 54.

The Q value changing unit 56 is disposed on the optical path of the resonator formed by the output mirror 54 and the rear mirror 55, and controls the Q value of the resonator. The Q value changing unit 56 is disposed, for example, between the output mirror 54 and the laser rod 51. Alternatively, the Q value changing unit 56 may be disposed between the rear mirror 55 and the laser rod 51. The Q value changing unit 56 includes a Q switch 57 and a polarizer 58. The Q switch 57 changes the Q value of the resonator according to an applied voltage. The Q switch 57 changes the polarization state of light transmitted therethrough according to the applied voltage. For example, an electro-optical element can be used.

For example, a Pockels cell can be used as the Q switch 57. The Q switch 57 changes the state of the resonator to a low Q state in a case where the applied voltage is a first voltage corresponding to Q switch OFF. The low Q state is a state in which the Q value of the resonator is lower than a laser oscillation threshold value. The first voltage is, for example, a voltage at which the first Q switch 57 functions as a quarter wavelength plate. The Q switch 57 changes the state of the resonator to a high Q state in a case where the applied voltage is a second voltage corresponding to Q switch ON. The high Q state is a state in which the Q value of the resonator is higher than the laser oscillation threshold value. The absolute value of the second voltage may be smaller than the absolute value of the first voltage, and the voltage may be a positive voltage or may be a negative voltage. The second voltage is, for example, 0 V (no voltage applied). In this case, the polarization state of light transmitted through the Q switch 57 does not change.

The polarizer 58 is disposed between the laser rod 51 and the Q switch 57. The polarizer 58 allows only linearly polarized light in a predetermined direction to pass therethrough. As the polarizer 58, for example, a beam splitter that transmits linearly polarized light in a predetermined direction (for example, p-polarized light) and reflects linearly polarized light in a direction perpendicular to the predetermined direction (for example, s-polarized light) can be used. The polarizer 58 may be omitted in a case where the laser rod 51 itself has polarized light selectivity, such as a case where alexandrite crystal is used as the laser rod 51.

Specifically, for the operation of the Q value changing unit 56, the Q switch 57 functions as a quarter wavelength plate in a case where the first voltage is applied to the Q switch 57. First, p-polarized light incident on the polarizer 58 from the laser rod 51 passes through the polarizer 58, and becomes circularly polarized light at the time of passing through the Q switch 57. Then, the light is reflected by the output mirror 54 and is incident on the Q switch 57 in an opposite direction. The circularly polarized light incident on the Q switch 57 in the opposite direction becomes linearly polarized light again at the time of passing through the Q switch 57, but is incident on the polarizer 58 as s-polarized light rotated by 90° and is emitted to the outside of the optical path of the resonator. On the other hand, in a case where the second voltage is applied to the Q switch 57, the p-polarized light incident on the polarizer 58 passes therethrough and further passes through the Q switch 57 without changing the polarization state. Thereafter, the p-polarized light is reflected by the output mirror 54, and the returned light also passes through the Q switch 57 without changing the polarization state, passes through the polarizer 58 transmitting the p-polarized light, and returns to the laser rod 51. Laser oscillation occurs by applying the second voltage in a state in which population inversion is sufficiently accumulated.

Figure 2:
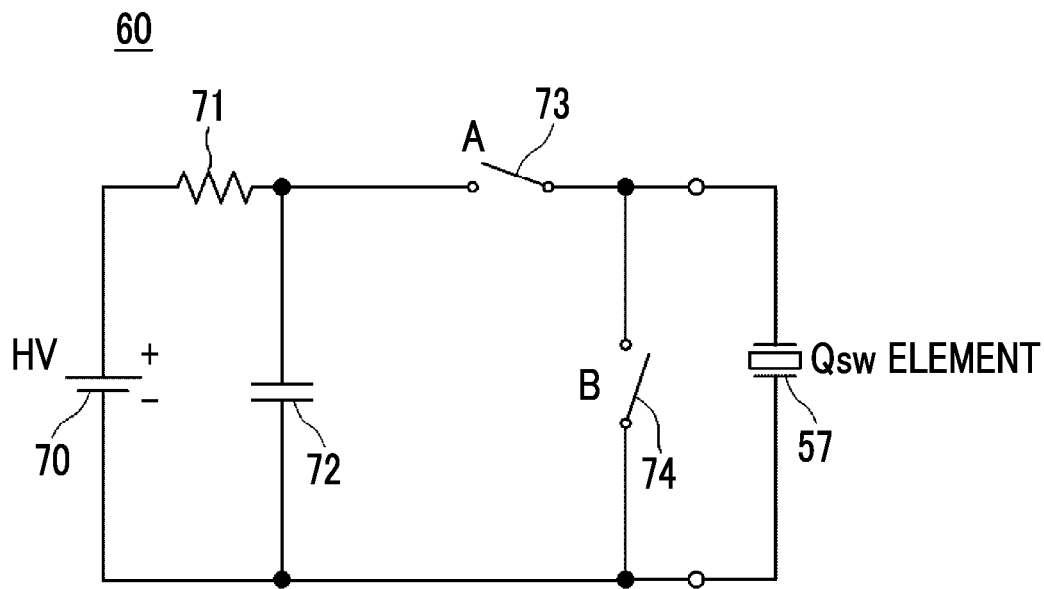
FIG. 2 is a schematic diagram of a Q switch driver of the laser device shown in FIG. 1.
Figure 3:
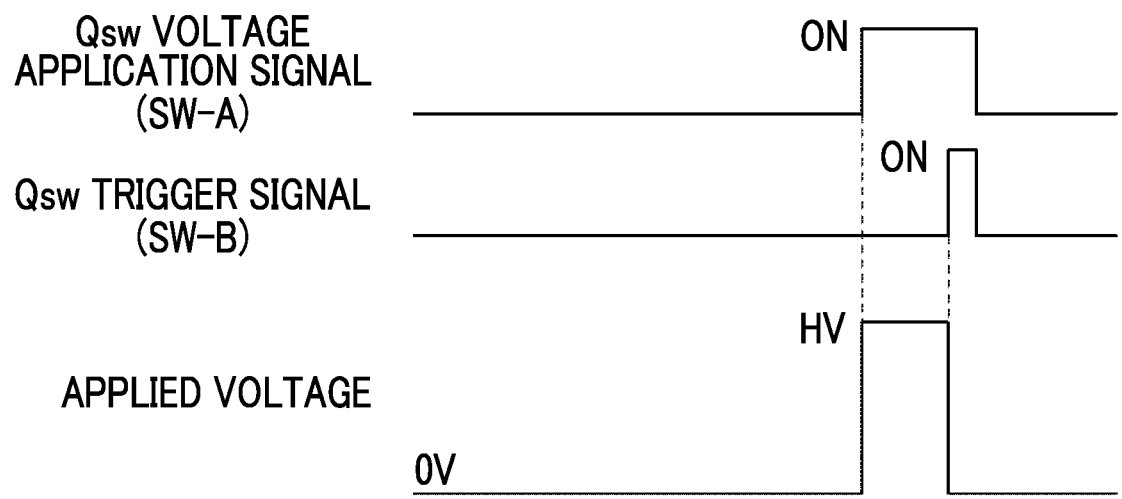
FIG. 3 is a timing chart showing the operation waveform of each component of the Q switch driver shown in FIG. 2.

The Q switch driver 60 applies a voltage to the Q switch 57 to drive the Q switch 57. Here, the Q switch driver 60 of the laser device 1 of the present embodiment will be described in detail with reference to the diagrams. FIG. 2 is a schematic diagram of a Q switch driver of the laser device of the present embodiment, and FIG. 3 is a timing chart showing the operation waveform of each component of the Q switch driver.

Here, an example is shown in which the first voltage is set to a predetermined high voltage (HV) and the second voltage is set to 0 V. As shown in FIG. 2, the Q switch driver 60 includes a high voltage power supply 70 for applying a voltage to the Q switch 57, a resistor 71 connected in series to the high voltage power supply 70, a capacitor 72 connected in parallel to the high voltage power supply 70, a first switch (SW-A) 73 connected in series to the high voltage power supply 70, and a second switch (SW-B) 74 connected in parallel to the high voltage power supply 70. As shown in FIG. 3, a first voltage (HV) is applied to the Q switch 57 by turning on only the first switch (SW-A) 73. The voltage application to the Q switch 57 is stopped by turning on the second switch (SW-B) 74 in this state.

Although the details will be described later, in the laser device 1 of the present embodiment, it is preferable to generate as large vibration as possible in the Q switch 57 at the time of applying the first voltage to the Q switch 57. In order to generate as large vibration as possible in Q switch 57, the rise time of the first voltage needs to be as sharp as possible. Therefore, by adopting the configuration described above, it is possible to obtain a sharp characteristic at both the rise time and the fall time of the first voltage. In particular, the rise time of the first voltage is preferably 2 μs or less, more preferably 1.5 μs or less, and even more preferably 1 μs or less.

The controller 61 controls the flash lamp power supply 59 and the Q switch driver 60 to emit excitation light to the laser rod 51 in a state in which the first voltage is applied to the Q switch 57 and change the voltage applied to the Q switch 57 from the first voltage to the second voltage after the emission of excitation light, thereby emitting pulsed laser light (giant pulse) L. The configuration of the hardware of the controller 61 is not particularly limited, and can be realized by appropriately combining a plurality of integrated circuits (ICs), processors, application specific integrated circuits (ASICs), field-programmable gate arrays (FPGAs), memories, and the like.

Figure 4:
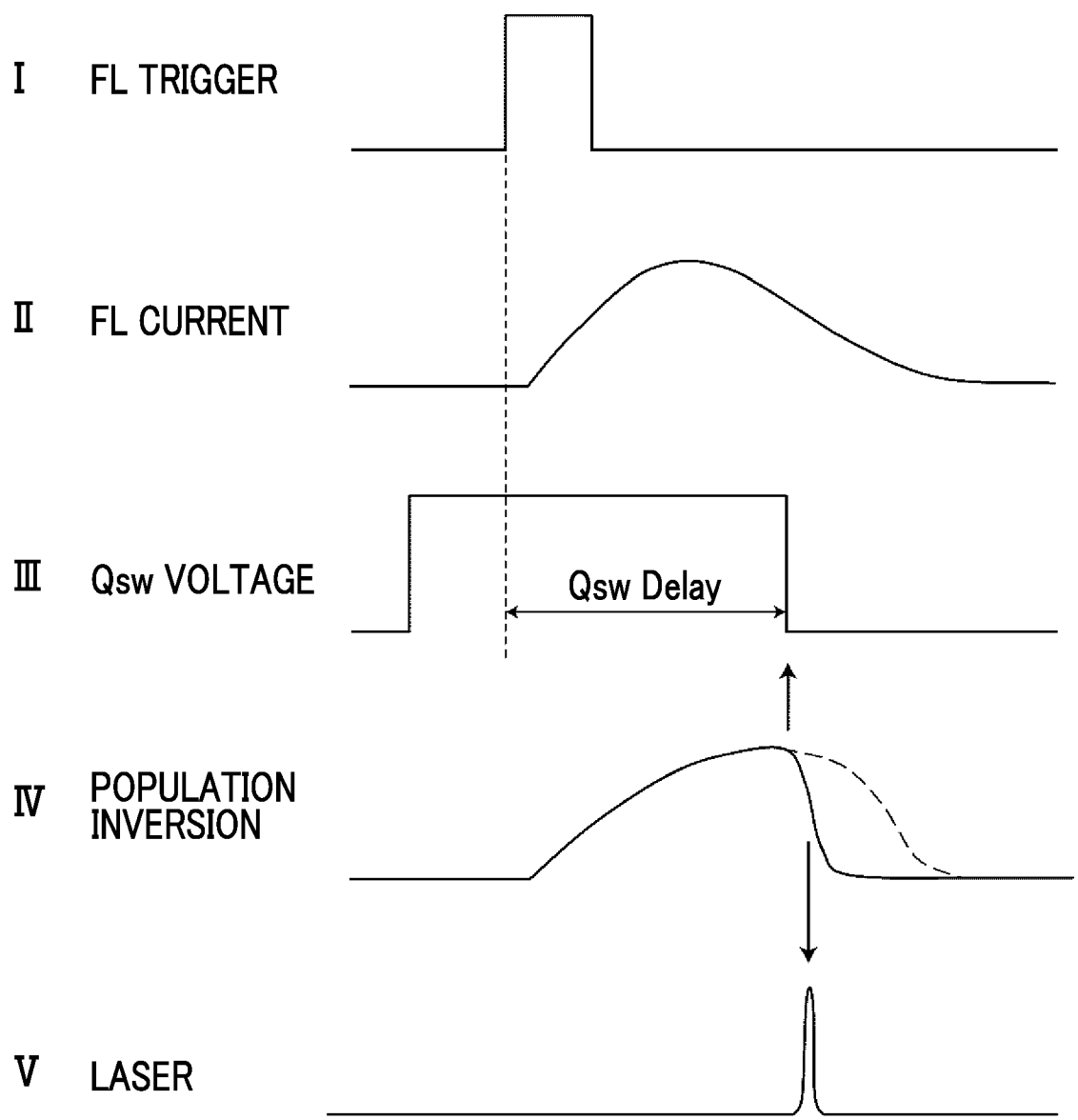
FIG. 4 is a timing chart showing the operation waveform of each component before timing adjustment of the laser device shown in FIG. 1.
Figure 5:
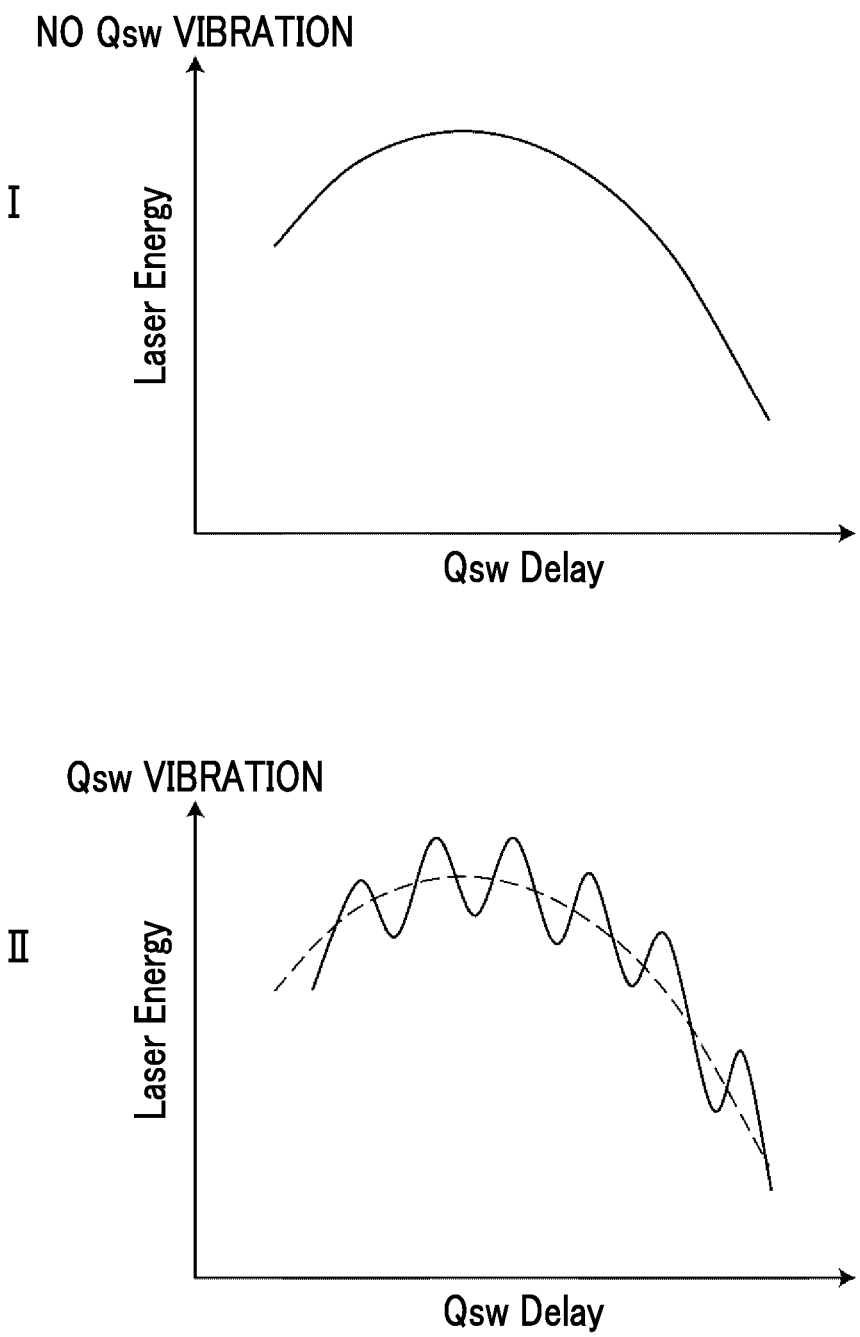
FIG. 5 is a graph showing the relationship between the Q switch ON timing and the pulse laser light intensity before timing adjustment in the laser device shown in FIG. 1.
Figure 7:
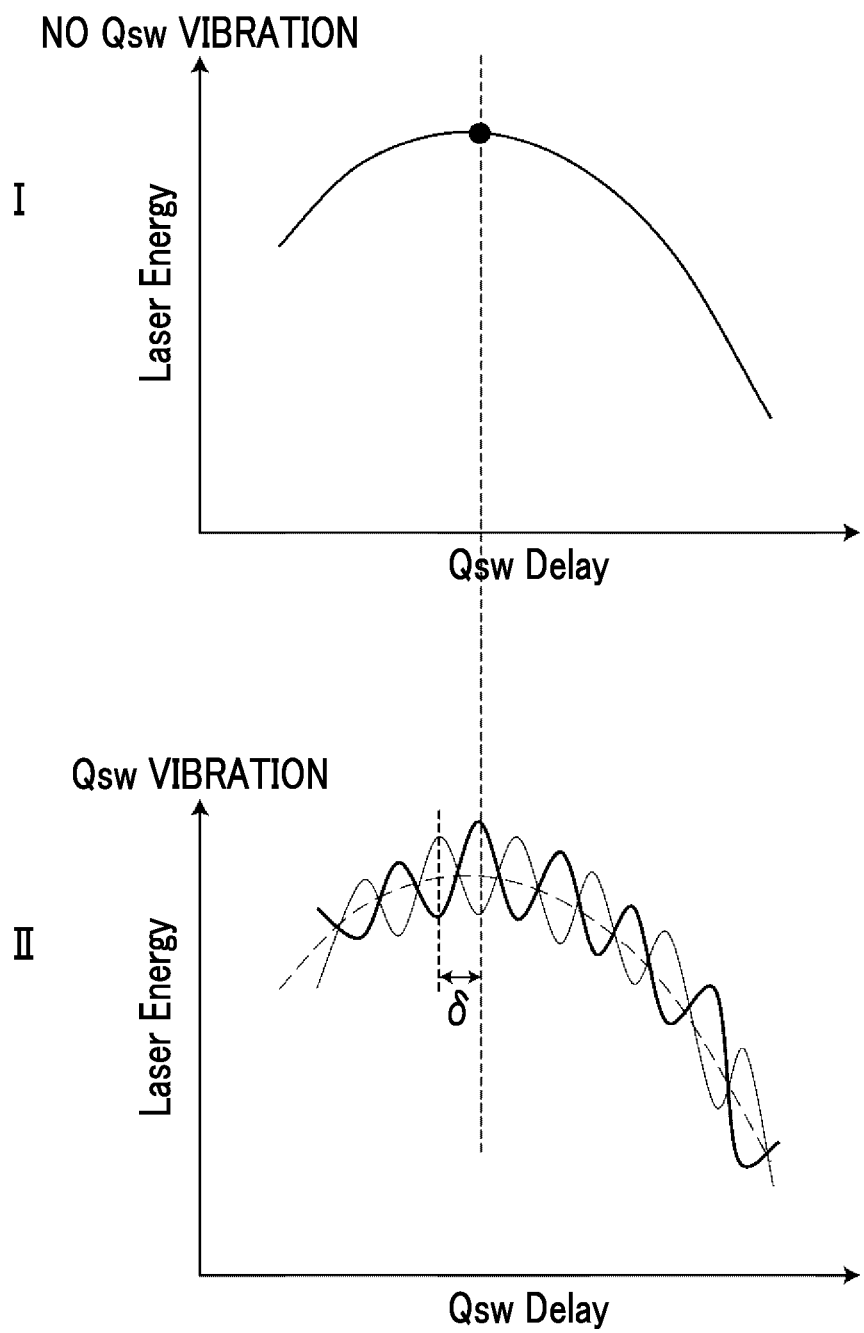
FIG. 7 is a graph showing the relationship between the Q switch ON timing and the pulse laser light intensity after timing adjustment in the laser device shown in FIG. 1.

Next, the operation of the laser device 1 of the present embodiment will be described in detail with reference to the diagrams. FIG. 4 is a timing chart showing the operation waveform of each unit before timing adjustment of the laser device 1 of the present embodiment. FIG. 5 is a graph showing the relationship between the Q switch ON timing and the pulsed laser light intensity before timing adjustment in the laser device 1. FIG. 6 is a timing chart showing the operation waveform of each unit after timing adjustment of the laser device 1. FIG. 7 is a graph showing the relationship between the Q switch ON timing and the pulsed laser light intensity after timing adjustment in the laser device 1.

In a case where a trigger signal for turning on the flash lamp 52 is turned on as shown in I of FIG. 4, the controller 61 drives the flash lamp power supply 59 as shown in II of FIG. 4. As shown in III of FIG. 4, the controller 61 controls the Q switch driver 60 so as to apply the first voltage corresponding to Q switch OFF to the Q switch 57 with the timing, at which the trigger signal for turning on the flash lamp 52 is turned on, as a reference. As shown in IV of FIG. 4, in a case where the flash lamp 52 is turned on, the amount of population inversion in the laser rod 51 increases. The controller 61 controls the Q switch driver 60 so as to apply the second voltage corresponding to Q switch ON to the Q switch 57 in a case where the amount of population inversion required for the generation of pulsed laser light (giant pulse) is exceeded. In the present embodiment, since the second voltage is 0 V, application of the second voltage is equivalent to stopping the voltage application. As shown in V of FIG. 4, in a case where the Q switch is turned on, laser light emitted from the laser rod 51 resonates in the resonator, and the pulsed laser light L is emitted from the pulsed laser light emission unit 50.

Here, the pulsed laser light intensity in the case of changing a delay time (denoted by Qsw Delay in FIGS. 4 to 7) until the Q switch is turned on from the application of the trigger signal theoretically shows the characteristic of a mountain shape as shown in I of FIG. 5. In practice, however, due to the vibration generated in the Q switch 57 at the time of applying the first voltage corresponding to Q switch off to the Q switch 57, the pulsed laser light intensity periodically changes around the characteristic of the mountain shape in I of FIG. 5 as shown in II of FIG. 5.

In the present embodiment, therefore, as shown in III of FIG. 6, first, the delay time until the Q switch is turned on from the application of the trigger signal is fixed to a preset time. As shown in IV of FIG. 6, the first voltage application start timing is set to a timing at which the intensity of pulsed laser light periodically changing due to the vibration of the Q switch 57 is maximized in a case where the preset first voltage application start timing is changed with a preset time width.

Specifically, in a case where the delay time is fixed to a certain delay time as shown in I of FIG. 7 and the first voltage application start timing is gradually changed as shown in IV of FIG. 6, the intensity of the pulsed laser light in the fixed delay time changes periodically as shown in II of FIG. 7.

Here, as shown in II of FIG. 7, by setting the first voltage application start timing to a timing at which the peak position of the period of the intensity change of the pulsed laser light matches the fixed delay time, that is, a timing at which the intensity of the pulsed laser light is maximized, the output of the pulsed laser light can be made higher than in a case where vibration is not generated in the Q switch 57 by using the vibration generated in the Q switch 57.

As described above, since the laser device 1 of the present embodiment makes the output of the pulsed laser light higher than in a case where vibration is not generated in the Q switch 57 by using the vibration generated in the Q switch 57, it is possible to increase the output of the pulsed laser light as the vibration generated in the Q switch 57 increases.

Since the vibration generated in the Q switch 57 attenuates with the passage of time, it is preferable that the time from the first voltage application timing (Q switch OFF) to Q switch ON is as short as possible. On the other hand, in a case where the first voltage corresponding to Q switch OFF is applied after the excitation light emission start timing, no population inversion is accumulated in the laser rod 51 during a period from the excitation light emission start timing to the first voltage application start timing. For this reason, power consumption and time during this period are wasted. Therefore, it is preferable that the preset first voltage application start timing is the same as the excitation light emission start timing. "The same as the excitation light emission start timing" referred to herein is assumed to include the range of ±20 μs from the excitation light emission start timing.

As shown in I of FIG. 7, it is preferable that the delay time is set to a time at which the intensity of the pulsed laser light is maximized in a case where, during a calibration operation different from the normal operation, the Q switch 57 is vibrated by applying the first voltage, emission of excitation light is started after the influence of the vibration of the Q switch 57 disappears, and then the time until the second voltage is applied to the Q switch is changed. In this manner, the output intensity of the pulsed laser light having the maximum efficiency can be obtained in addition to increasing the output of the pulsed laser light using the vibration generated in the Q switch 57.

Here, in order to eliminate the influence of the vibration of the Q switch 57, the first voltage application start timing may be set to be considerably earlier than the excitation light emission start timing. As a result, since the vibration generated in the Q switch 57 at the time of application of the first voltage attenuates and disappears, it is possible to eliminate the influence of the vibration of the Q switch 57 at the time of emission of the pulsed laser light. Specifically, the first voltage application start timing may be set to be earlier than the excitation light emission start timing by about 1 ms. In addition to changing the first voltage application start timing, by increasing the rise time of the first voltage, it is possible to suppress the vibration itself generated in the Q switch 57. Therefore, during the calibration operation, the change of the first voltage application start timing and the change of the rise time of the first voltage may be combined to eliminate the influence of the vibration of the Q switch 57.

Assuming that the period of the intensity change of the pulsed laser light in the case of changing the first voltage application start timing is T, a time width (preset time width) in which the first voltage application start timing is changed in order to determine the first voltage application start timing during the normal operation can be expressed as nT+δ. Here, n is an integer, and δ is a time less than the period T. For the preset time width, since it is possible to specify the peak position of the period of the intensity change of the pulsed laser light by checking the time of one period, it is preferable to adopt such a mode.

Figure 8:
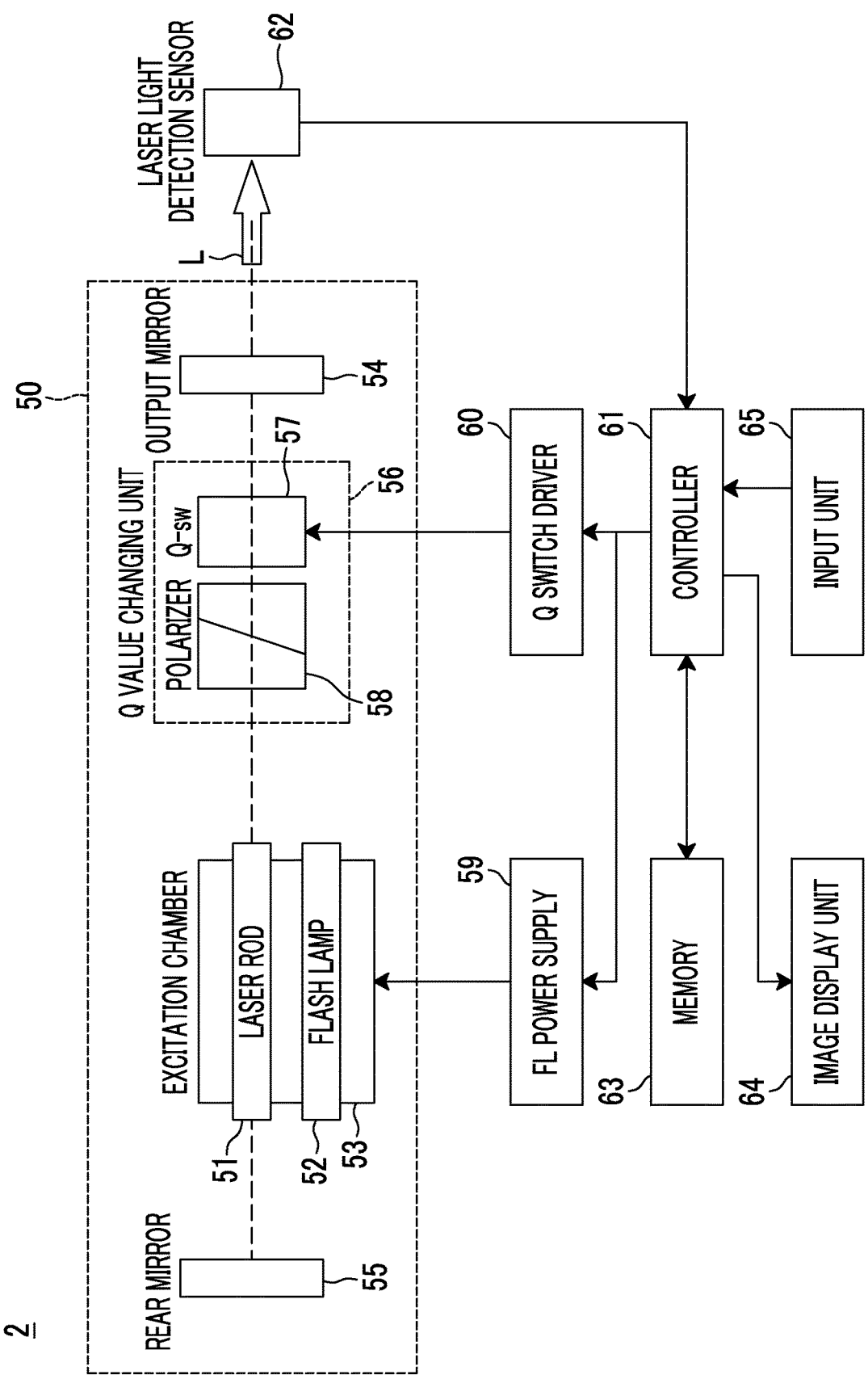
FIG. 8 is a block diagram showing a laser device of a second embodiment of the present invention.

Next, a second embodiment of the laser device of the present invention will be described. FIG. 8 is a diagram showing the schematic configuration of a laser device 2 of the second embodiment. The laser device 2 of the second embodiment is configured to be able to further change the first voltage application start timing set in the laser device 1 of the first embodiment. By making it possible to further change the first voltage application start timing as described above, an operator can adjust the first voltage application start timing again even in a case where the first voltage application start timing, at which the intensity of the pulsed laser light L is maximized, is shifted due to, for example, environmental influences or aging.

Specifically, the laser device 2 of the second embodiment further includes a laser light detection sensor 62 as a detection unit, a memory 63 as a storage unit, an image display unit 64, and an input unit 65. Other configurations are the same as the configurations in the laser device 1 of the first embodiment.

The laser light detection sensor 62 detects the intensity of the pulsed laser light L emitted from the resonator. Specifically, the laser light detection sensor 62 includes a light detection element, such as a photodiode.

A periodic change in the intensity of the pulsed laser light L caused by the vibration of the Q switch 57 described above is stored in advance in the memory 63. That is, as shown in II of FIG. 7, the relationship (hereinafter, referred to as a periodic characteristic of the pulsed laser light L) between the delay time and the intensity of the pulsed laser light L at the set first voltage application start timing is stored in advance in the memory 63.

The input unit 65 receives a change in the first voltage application start timing by the operator. In the present embodiment, the input unit 65 corresponds to a timing changing unit of the present invention.

In response to the instruction input through the input unit 65, the controller 61 reads out the periodic characteristic of the pulsed laser light L stored in the memory 63, and displays the read periodic characteristic on the image display unit 64. In the present embodiment, the controller 61 corresponds to a display controller of the present invention.

The image display unit 64 displays the periodic characteristic of the pulsed laser light L as described above, and is, for example, a liquid crystal touch panel also serving as the input unit 65.

The intensity of the pulsed laser light L detected by the laser light detection sensor 62 is output to the controller 61. The controller 61 stores the input intensity of the pulsed laser light L and the first voltage application start timing used in acquiring the pulsed laser light L in the memory 63 so as to be associated with each other. The controller 61 stores the above-described periodic characteristic of the pulsed laser light L in the memory 63 by storing the first voltage application start timing and the intensity of the pulsed laser light L detected by the laser light detection sensor 62 in the memory 63 so as to be sequentially associated with each other while changing the first voltage application start timing. In a case where the laser device 2 is actually used, the laser light detection sensor 62 is retracted from the optical path of the pulsed laser light L.

In the laser device 2 of the second embodiment, for example, in the case of calibrating the first voltage application start timing, the operator inputs an instruction to perform the calibration using the input unit 65.

In a case where an instruction input for calibration is received through the input unit 65, the controller 61 sequentially acquires the intensity of the pulsed laser light L corresponding to the first voltage application start timing while changing the first voltage application start timing and stores the intensity of the pulsed laser light L in the memory 63, thereby storing the periodic characteristic of the pulsed laser light L.

Then, the controller 61 reads out the periodic characteristic of the pulsed laser light L stored in the memory 63, and displays the read periodic characteristic on the image display unit 64. In addition, the controller 61 displays an index indicating the first voltage application start timing, which is currently set, on the image display unit 64.

The operator checks the relationship between the periodic characteristic of the pulsed laser light L and the currently set first voltage application start timing, which are displayed on the image display unit 64, and changes the currently set first voltage application start timing using the input unit 65. Specifically, the operator changes the setting so that the first voltage application start timing becomes the maximum value of the periodic characteristic of the pulsed laser light L.

Figure 9:
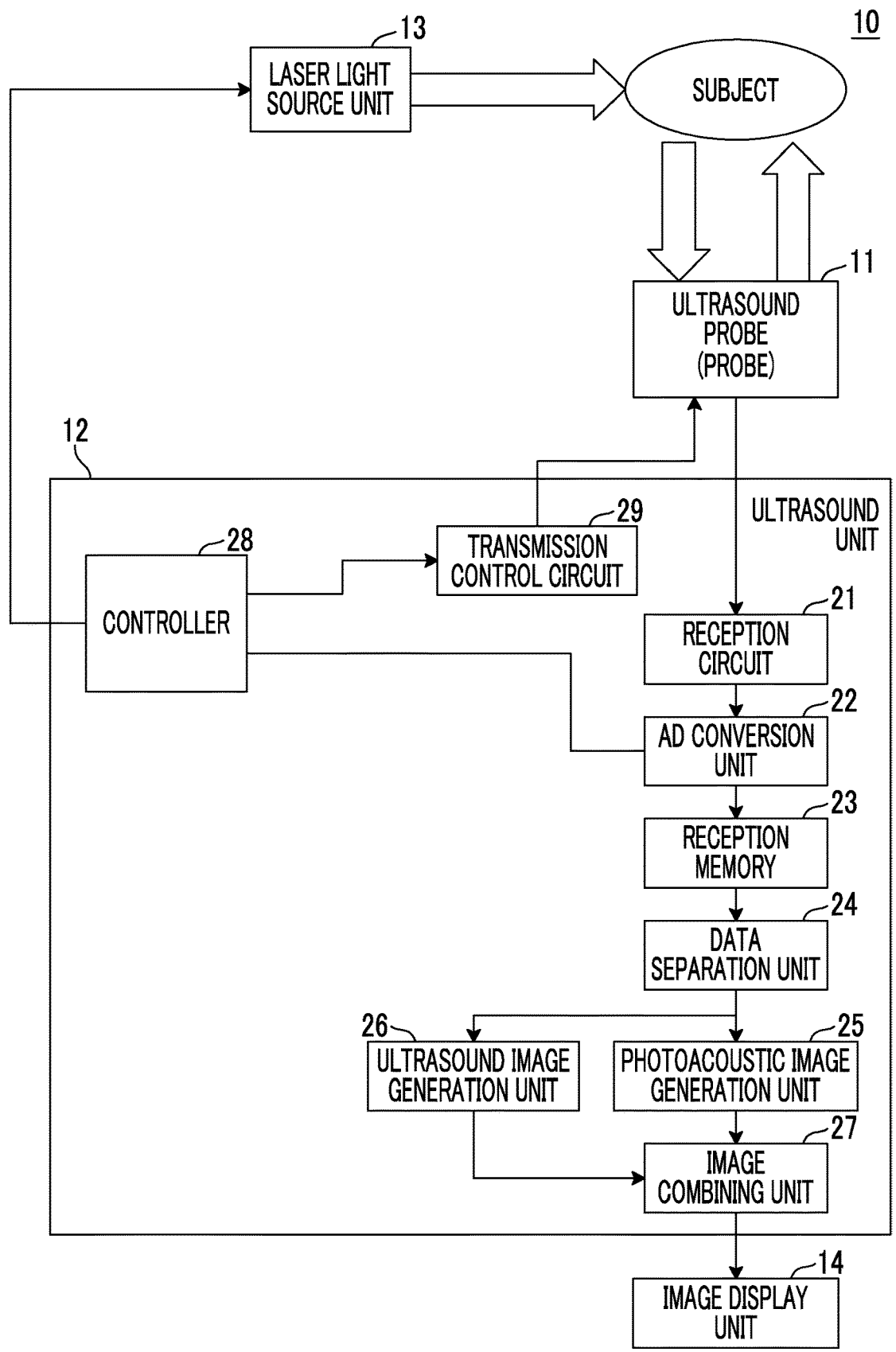
FIG. 9 is a block diagram showing a photoacoustic measurement apparatus including the laser device of an embodiment of the present invention.

Next, a photoacoustic measurement apparatus including an embodiment of the laser device of the present invention will be described. FIG. 9 is a diagram showing the schematic configuration of the photoacoustic measurement apparatus.

A photoacoustic measurement apparatus 10 includes an ultrasound probe (probe) 11, an ultrasound unit 12, and a laser light source unit 13. In the present embodiment, an ultrasound wave is used as an acoustic wave. However, the present invention is not limited to the ultrasound wave, and an acoustic wave having an audible frequency may be used as long as an appropriate frequency can be selected according to an examination target, measurement conditions, or the like.

The laser light source unit 13 includes the laser device of the first or second embodiment. The pulsed laser light L emitted from the laser light source unit 13 is guided to the probe 11 by using, for example, light guiding means such as an optical fiber, and is emitted from the probe 11 to the subject. The emission position of the pulsed laser light L is not particularly limited, and the pulsed laser light L may be emitted from a place other than the probe 11.

Within the subject, ultrasound waves (acoustic waves) are generated due to a light absorber absorbing the energy of the emitted pulsed laser light L. The probe 11 has a plurality of ultrasound transducers arranged in a one-dimensional manner, for example. The probe 11 detects acoustic waves (photoacoustic waves) from the inside of the subject with a plurality of ultrasound transducers arranged in a one-dimensional manner, and outputs a photoacoustic wave signal. The probe 11 transmits acoustic waves (ultrasound waves) to the subject, detects reflected acoustic waves (reflected ultrasound waves) from the subject with respect to the transmitted ultrasound waves, and outputs a reflected wave signal. The probe 11 is not limited to the linear probe, but may be a convex probe or a sector probe.

The ultrasound unit 12 has a reception circuit 21, an analog to digital convertor (AD converter) 22, a reception memory 23, a data separation unit 24, a photoacoustic image generation unit 25, an ultrasound image generation unit 26, an image combining unit 27, a controller 28, and a transmission control circuit 29. The ultrasound unit 12 typically has a processor, a memory, a bus, and the like. Programs relevant to photoacoustic image generation and ultrasound image generation are installed on the memory of the ultrasound unit 12. By running the programs using the controller 28 configured by a processor, functions of the data separation unit 24, the photoacoustic image generation unit 25, the ultrasound image generation unit 26, and the image combining unit 27 are realized. That is, each of these units is formed by the memory on which the programs are installed and the processor.

The configuration of the hardware of the ultrasound unit 12 is not particularly limited, and can be realized by appropriately combining a plurality of integrated circuits (ICs), processors, application specific integrated circuits (ASICs), field-programmable gate arrays (FPGAs), memories, and the like.

The reception circuit 21 receives the photoacoustic wave signal output from the probe 11. In addition, the reflected wave signal output from the probe 11 is received. Typically, the reception circuit 21 includes a low noise amplifier, a variable gain amplifier, and a low pass filter. The photoacoustic wave signal and the reflected wave signal output from the probe 11 are amplified by the low noise amplifier, and then the gain is adjusted according to the depth by the variable gain amplifier and high frequency components are cut by the low pass filter.

The AD converter 22 converts the photoacoustic wave signal and the reflected wave signal received by the reception circuit 21 into digital signals. The AD converter 22 samples the photoacoustic wave signal and the reflected wave signal at predetermined sampling periods based on, for example, a sampling clock signal having a predetermined period. The AD converter 22 stores the sampled photoacoustic wave signal and reflected wave signal (sampling data) in the reception memory 23. The reception circuit 21 and the AD converter 22 may be formed as, for example, one IC, or may be formed as individual ICs.

The data separation unit 24 separates the pieces of sampling data of the photoacoustic wave signal and the reflected wave signal, which are stored in the reception memory 23, from each other. The data separation unit 24 inputs the sampling data of the photoacoustic wave signal to the photoacoustic image generation unit 25. In addition, the separated sampling data of the reflected wave signal is input to the ultrasound image generation unit 26. In the present embodiment, the photoacoustic image generation unit 25 and the ultrasound image generation unit 26 correspond to an acoustic wave image generation unit of the present invention.

The photoacoustic image generation unit 25 generates a photoacoustic image based on the photoacoustic wave signal output from the probe 11. The generation of a photoacoustic image includes, for example, image reconstruction such as phase matching addition, detection, and logarithmic conversion. The ultrasound image generation unit 26 generates an ultrasound image (reflected acoustic wave image) based on the reflected wave signal output from the probe 11. The generation of an ultrasound image also includes image reconstruction such as phase matching addition, detection, and logarithmic conversion.

The image combining unit 27 combines the photoacoustic image and the ultrasound image. The image combining unit 27 performs image combination by superimposing the photoacoustic image and the ultrasound image on each other, for example. The composite image is displayed on the image display unit 14, such as a display. Without performing image combination, the photoacoustic image and the ultrasound image may be displayed on the image display unit 14 side by side or the photoacoustic image and the ultrasound image may be switched and displayed.

The controller 28 controls each unit in the ultrasound unit 12. The controller 28 transmits a trigger signal to the laser light source unit 13, for example. In a case where the trigger signal is received, the controller 61 (FIG. 1) of the laser light source unit 13 turns on the flash lamp 52, and then changes the voltage applied to the Q switch 56 from the first voltage to the second voltage and emits the pulsed laser light L. The controller 28 controls the sampling start timing of the photoacoustic wave signal by transmitting a sampling trigger signal to the AD converter 22 in response to the emission of the pulsed laser light L.

In the case of generating an ultrasound image, the controller 28 transmits an ultrasound wave transmission trigger signal for giving an instruction of ultrasound wave transmission to the transmission control circuit 29. In a case where the ultrasound wave transmission trigger signal is received, the transmission control circuit 29 makes the probe 11 transmit ultrasound waves. The controller 28 transmits a sampling trigger signal to the AD converter 22 according to the timing of ultrasound wave transmission, thereby starting the sampling of the reflected wave signal.

In the above embodiments, a case has been described in which the probe 11 in the photoacoustic measurement apparatus 10 detects both the photoacoustic wave and the reflected ultrasound wave. However, a probe used to generate an ultrasound image and a probe used to generate a photoacoustic image do not necessarily need to be the same. The photoacoustic wave and the reflected ultrasound wave may be detected by separate probes. In the above embodiments, an example in which the laser device forms a part of the photoacoustic measurement apparatus has been described. However, the present invention is not limited thereto. The laser device of the present invention can be used for an apparatus different from the photoacoustic measurement apparatus.

While the present invention has been described based on the preferred embodiments, the laser device and the photoacoustic measurement apparatus of the present invention are not limited only to the above embodiments, and various modifications and changes in the configurations of the above embodiments are also included in the range of the present invention.

With regard to the above-described embodiments, the following appendixes will be further disclosed.

(Appendix 1)

A laser device, comprising:

an excitation light source that emits excitation light;

a laser medium that receives the excitation light emitted from the excitation light source and emits laser light;

a resonator that includes a pair of mirrors with the laser medium interposed therebetween and that emits pulsed laser light by resonating the laser light between the pair of mirrors;

a Q switch that is disposed on an optical path of the resonator to change a Q value of the resonator according to an applied voltage and that makes a Q value of the resonator in a case where a first voltage is applied lower than a Q value of the resonator in a case where a second voltage different from the first voltage is applied;

a Q switch driving unit that drives the Q switch by applying the first voltage and the second voltage to the Q switch; and a processor that controls the excitation light source and the Q switch driving unit to emit the excitation light to the laser medium in a state in which the first voltage is applied to the Q switch and change a voltage applied to the Q switch from the first voltage to the second voltage after the emission of the excitation light such that the pulsed laser light is emitted, wherein, during a normal operation, the processor applies the first voltage to vibrate the Q switch and applies the second voltage to the Q switch at a timing at which a preset delay time has passed from start of the emission of the excitation light, and an application start timing of the first voltage during the normal operation is set to a timing at which an intensity of the pulsed laser light periodically changing due to vibration of the Q switch is maximized in a case where the preset application start timing of the first voltage is changed with a preset time width.

(Appendix 2)

The laser device according to Appendix 1, wherein the processor is a circuitry.

What is claimed is:

1. A laser device; comprising:

an excitation light source that emits excitation light;

a laser medium that receives the excitation light emitted from the excitation light source and emits laser light;

a resonator that includes a pair of mirrors with the laser medium interposed therebetween and that emits pulsed laser light by resonating the laser light between the pair of mirrors;

a Q switch that is disposed on an optical path of the resonator to change a Q value of the resonator according to an applied voltage and that makes a Q value of the resonator in a case where a first voltage is applied lower than a Q value of the resonator in a case where the first voltage is not applied;

a Q switch driver that supplies the first voltage to the Q-switch; and a controller that controls the excitation light source and the Q switch driving unit to emit the excitation light to the laser medium in a state in which the first voltage is applied to the Q switch and stop supplying the first voltage to the Q-switch after the emission of the excitation light such that the pulsed laser light is emitted, wherein, during a normal operation, the controller applies the first voltage to vibrate the Q switch and does not apply the first voltage to the Q switch at a timing at which a preset delay time has passed from start of the emission of the excitation light, and an application start timing of the first voltage during the normal operation is set to a timing at which an intensity of the pulsed laser light periodically changing due to vibration of the Q switch is maximized in a case where a preset application start timing of the first voltage is changed with a preset time width.

2. The laser device according to claim 1, wherein the preset application start timing of the first voltage is the same as an emission start timing of the excitation light.

3. The laser device according to claim 1, wherein the delay time is set to a time at which the intensity of the pulsed laser light is maximized in a case where, during a calibration operation different from the normal operation, the Q switch is vibrated by applying the first voltage, emission of the excitation light is started after an influence of the vibration of the Q switch disappears, and then a time until the stop of the supply of the first voltage to the Q switch is changed.

4. The laser device according to claim 1, wherein the preset time width is the same time as a period of an intensity change of the pulsed laser light in a case where the application start timing of the first voltage is changed.

5. The laser device according to claim 1, wherein a rise time of the first voltage is 2 μs or less.

6. The laser device according to claim 5, wherein the rise time of the first voltage is 1 μs or less.

7. The laser device according to claim 1, further comprising:
a storage unit that stores characteristic information indicating characteristics of a periodic change in the intensity of the pulsed laser light due to vibration of the Q switch in a case where the application start timing of the first voltage is changed.

8. The laser device according to claim 7, further comprising:
a display controller that displays the characteristic information stored in the storage unit on a display unit.

9. The laser device according to claim 1, further comprising:
a detection unit that detects a periodic change in the intensity of the pulsed laser light.

10. The laser device according to claim 1, further comprising:
a timing changing unit that receives a change in the application start timing of the first voltage during the normal operation.

11. A photoacoustic measurement apparatus, comprising:
the laser device according to claim 1; and
a probe that detects photoacoustic waves generated in a subject due to emission of laser light from the laser device and outputs a photoacoustic wave signal.

12. The photoacoustic measurement apparatus according to claim 11, further comprising:
an acoustic image generation unit that generates a photoacoustic image based on the photoacoustic wave signal output from the probe.

13. The photoacoustic measurement apparatus according to claim 12,
wherein the probe detects a reflected wave of an acoustic wave transmitted to the subject and outputs a reflected wave signal, and
the acoustic image generation unit generates a reflected acoustic image based on the reflected wave signal.

* * * * *